United States Patent
Palti et al.

(10) Patent No.: US 6,811,535 B2
(45) Date of Patent: Nov. 2, 2004

(54) DEVICE FOR MONITORING A VITAL SIGN

(75) Inventors: Yoram Palti, Haifa (IL); Yoram Wasserman, Haifa (IL); Israel Urbach, Haifa (IL); Baruch Glick, Haifa (IL); Aviran Itzhaki, Haifa (IL); Doron Kopel, Zechron J'Aakov (IL)

(73) Assignee: Koninklijke Philips Electronics N.V., Eindhoven (NL)

( * ) Notice: Subject to any disclaimer, the term of this patent is extended or adjusted under 35 U.S.C. 154(b) by 67 days.

(21) Appl. No.: 09/862,290

(22) Filed: May 22, 2001

(65) Prior Publication Data

US 2001/0056240 A1 Dec. 27, 2001

(30) Foreign Application Priority Data

Jun. 14, 2000 (EP) .......................................... 00202064

(51) Int. Cl.[7] .................................................. A61B 5/02
(52) U.S. Cl. ...................................... 600/499; 600/503
(58) Field of Search ................................ 600/499, 500, 600/501, 502, 503, 481

(56) References Cited

U.S. PATENT DOCUMENTS

| | | | | | |
|---|---|---|---|---|---|
| 4,667,672 A | * | 5/1987 | Romanowski | .............. | 128/327 |
| 4,850,369 A | * | 7/1989 | Yamasawa | .................. | 128/680 |
| 4,862,895 A | * | 9/1989 | Yamasawa | .................. | 128/680 |
| 4,951,679 A | * | 8/1990 | Harada | ........................ | 600/485 |
| 4,976,268 A | * | 12/1990 | Kurosawa et al. | .......... | 600/500 |
| 4,987,900 A | * | 1/1991 | Eckerle et al. | ............... | 600/485 |
| 5,351,694 A | * | 10/1994 | Davis et al. | ................. | 128/672 |
| 5,396,895 A | * | 3/1995 | Takashima et al. | ......... | 128/687 |
| 5,494,043 A | * | 2/1996 | O'Sullivan et al. | ......... | 128/687 |
| 5,617,867 A | * | 4/1997 | Butterfield et al. | ......... | 128/672 |
| 5,795,300 A | * | 8/1998 | Bryars | ........................ | 600/500 |
| 5,876,346 A | * | 3/1999 | Corso | ......................... | 600/485 |
| 5,984,874 A | * | 11/1999 | Cerwin | ....................... | 600/549 |
| 6,290,650 B1 | * | 9/2001 | Butterfield et al. | ......... | 600/485 |
| 6,336,901 B1 | * | 1/2002 | Itonaga et al. | .............. | 600/499 |
| 6,379,310 B1 | * | 4/2002 | Mori et al. | .................. | 600/490 |
| 6,440,081 B1 | * | 8/2002 | Yang | ........................... | 600/503 |
| 2002/0156382 A1 | * | 10/2002 | Freund et al. | .............. | 600/490 |
| 2002/0188209 A1 | * | 12/2002 | Ogura | ........................ | 600/490 |

FOREIGN PATENT DOCUMENTS

| | | | | |
|---|---|---|---|---|
| EP | 0956812 A1 | | 11/1999 | |
| EP | 1048267 A1 | * | 11/2000 | ........... A61B/5/022 |

* cited by examiner

*Primary Examiner*—James Hook
(74) *Attorney, Agent, or Firm*—Ernestine C. Bartlett

(57) ABSTRACT

A device (1) for monitoring a vital sign of a living subject, comprising a measuring unit (2) for measuring at least one physical quantity indicative of said vital sign at an area (8) overlying an artery (7) of the subject, which measuring unit (2) is provided on a carrier (3) to be worn by the subject during operation, and a processing unit (4) for processing the measured physical quantity into a value for the vital sign, which device (1) is provided with at least one detector (5) for detecting the position of the measuring unit (2) relative to the artery (7) of the subject during operation and for actuating a feedback signal (Ufeedback) in dependence on this position. The user can move the device (1) relative to the artery (7) until the feedback signal (Ufeedback) is given, and thus a correct positioning of the measuring unit (2) relative to the artery (7) is achieved in an easy manner.

12 Claims, 4 Drawing Sheets

DEVICE FOR MONITORING A VITAL SIGN

Figure 1:
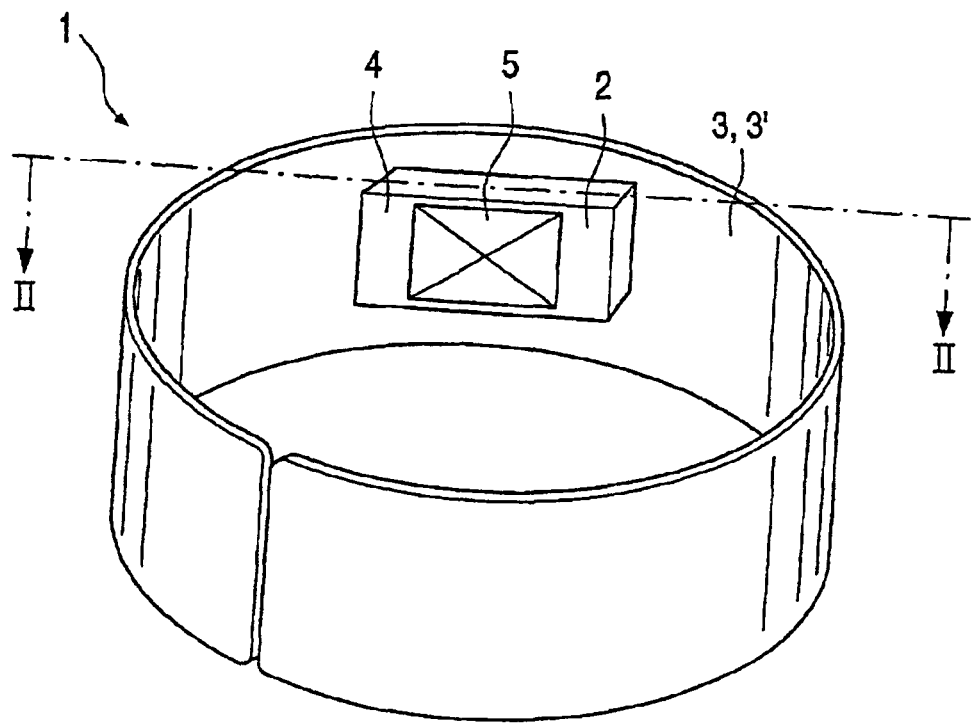

The invention relates to a device for monitoring a vital sign of a living subject, comprising a measuring unit for measuring at least one physical quantity indicative of said vital sign at an area overlying an artery of the subject, which measuring unit is provided on a carrier to be worn by the subject during operation, and a processing unit for processing the measured physical quantity into a value for the vital sign.

A device of the type defined in the opening paragraph is known from U.S. Pat. No. 4,660,566.

The known device is a device for monitoring a vital sign, the vital sign monitored by this device being a blood pressure of a subject. The known device comprises a measuring unit comprising a sensor provided on an inflatable cushion, and a processing unit. This cushion is provided on a carrier comprising a bracelet of flexible material worn by a user around his or her wrist. The sensor measures a physical quantity indicative of the blood pressure at an area overlying an artery of the subject. To measure the physical quantity effectively, the sensor on the cushion has to be positioned correctly relative to the artery. Therefore the sensor on the cushion is positioned relative to the artery on the wrist during operation, by means of a strap which is wound around the thumb of the subject and which is interlocked with a strip on the bracelet. Further locking strips are attached to the flexible bracelet to maintain the bracelet in this position. In this known device, pressure pulses are applied by means of the cushion to a local, discrete external point overlying the radial artery of the subject so as to effect a blocking or an unblocking condition of the artery. When the sensor detects said condition, the instantaneous value of the pressure in the cushion is measured, for providing through the processing unit a value of said subject's blood pressure. A disadvantage of the known device is that a correct positioning of the sensor relative to the artery is not guaranteed, and thus a "correct" measurement could in fact be incorrect. This is highly undesirable both in the monitoring of a vital sign by a professional in a professional situation, and in a domestic situation, where the measurement is carried out by a person him- or herself.

It is an object of the invention to provide an improved device for monitoring a vital sign of a subject which is easy to use and is correctly placeable relative to the artery.

To achieve this object, a device according to the invention is characterized in that the device is provided with at least one detector for detecting the position of the measuring unit relative to the artery of the subject during operation and for actuating a feedback signal in dependence on this position. A user of the device knows that a correct position of the measuring unit relative to the artery is reached when the feedback signal is given. The user can move the device relative to the artery until the feedback signal is given, and thus a correct positioning of the measuring unit relative to the artery is achieved in an easy manner. Next to that, the structure of the device is simpler, because no additional fastening parts are necessary in the device for achieving a correct positioning of the measuring unit. An embodiment of a device in accordance with the invention is characterized in that the detector comprises at least one sensor for detecting the presence of the artery in the vicinity of the sensor, which sensor is chosen from a group comprising electro-optical sensors and ultrasound sensors. These sensors work efficiently and can be easily integrated within the device, while the comfort of use of the device is maintained.

It is furthermore advantageous when a plurality of sensors for detecting the presence of the artery in the vicinity of the sensor are provided in an array. One given sensor in the array will detect the presence of the artery in the case of a correct position of the measuring unit relative to the artery. A number of sensors in the array will not detect the presence of the artery, but at least one sensor will when the device is placed with its measuring unit on the artery. Thus an indication can be given to the user through the sensors in which directions the device should be moved for said given sensor to detect the presence of the artery. Furthermore, the detector can be varied with respect to its structure and size through combining of arrays of sensors, depending on the type of device for monitoring vital signs in which the detector is applied.

An embodiment of a device in accordance with the invention is characterized in that the feedback signal is chosen from a group comprising audio and visual signals. Audio and visual signals are easily recognizable for users. Furthermore, the freedom is created to adapt the feedback signal to the demands of the varying types of devices for monitoring vital signs and to the demands of varying user groups of the device.

It is advantageous when the carrier comprises an annular body which is at least partly rigid, and especially when the annular body is entirely rigid. The rigid annular body simplifies the placement of the measuring unit on the subject whose vital signs are to be monitored. The rigid annular body has a fixed shape corresponding to the body part of the subject it is to be placed on, so that its placement can be performed in a clear and unambiguous way. Next to that, the rigid annular body contributes to the correct positioning of the measuring unit relative to the artery of the subject. It offers a first rough positioning of the annular body with the measuring unit on the subject, while the positioning of the measuring unit relative to the artery of the subject is further refined by shifting of the annular body relative to the artery over small distances in reaction to the feedback signal actuated by the detector. Furthermore, particularly if the measuring unit comprises an inflatable cushion, the rigid annular body bounds the level of expansion of the inflatable cushion, so that the cushion cannot be excessively inflated during operation. This benefits an effective application of pressure by the cushion to the area overlying the artery.

An embodiment of a device in accordance with the invention is characterized in that the measuring unit comprises an inflatable cushion for applying a pressure to said area overlying said artery of the subject, and the cushion comprises a plurality of separately inflatable cushion parts. During operation each cushion part can apply pressure locally on said area overlying said artery of the subject. The transmission of said pressure is thus less disturbed by the structure of the area, comprising bones and tendons, because the cushion parts can enter between the bones and tendons. Once the cushion has been positioned correctly relative to the artery with use of the detector, this pressure is applied to the area overlying the artery of the subject in an efficient way.

An embodiment of a device in accordance with the invention is characterized in that the cushion parts comprise protuberances, projecting from a surface area of the carrier in a direction practically perpendicular to that surface area. In this way, the separately inflatable cushion parts are finger-shaped elements protruding from the carrier, which benefits an efficient application of local pressure by each cushion part to said area overlying said artery of the subject.

With the cushion comprising a plurality of separately inflatable cushion parts, it is advantageous when the carrier comprises an annular body which can be closed during operation, and when the cushion is provided along an entire inner wall of said body. The cushion parts penetrating between bones and tendons are also advantageous for applying an annular pressure to an extremity of a subject, as in known other blood pressure monitors.

Figure 2:
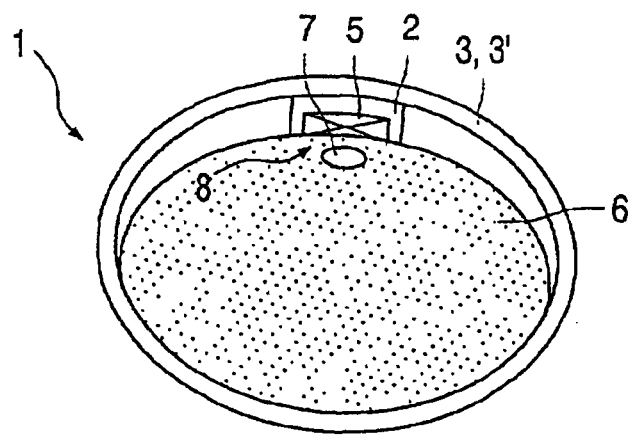
Figure 3A:
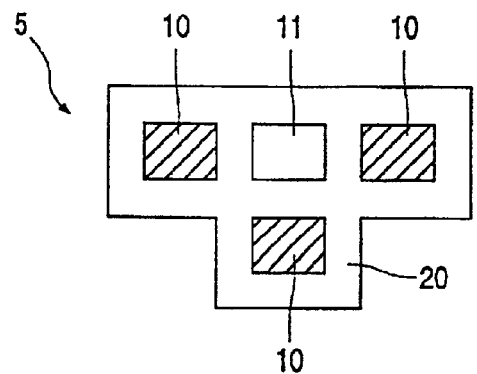
Figure 3B:
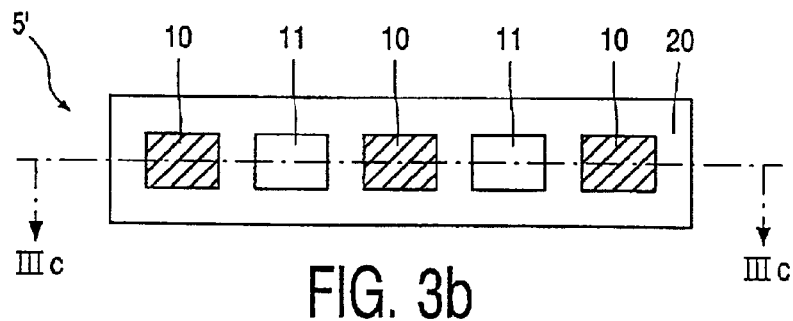
Figure 3C:
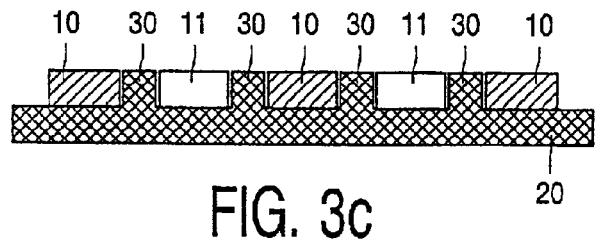
Figure 4:
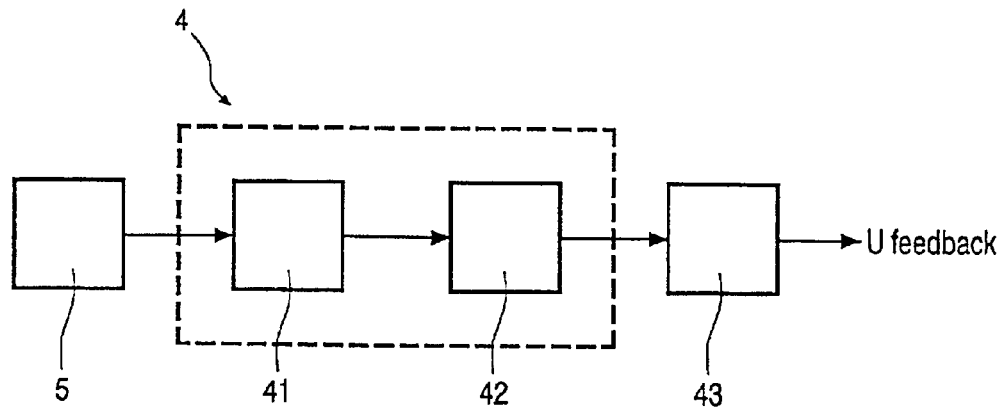
Figure 5:
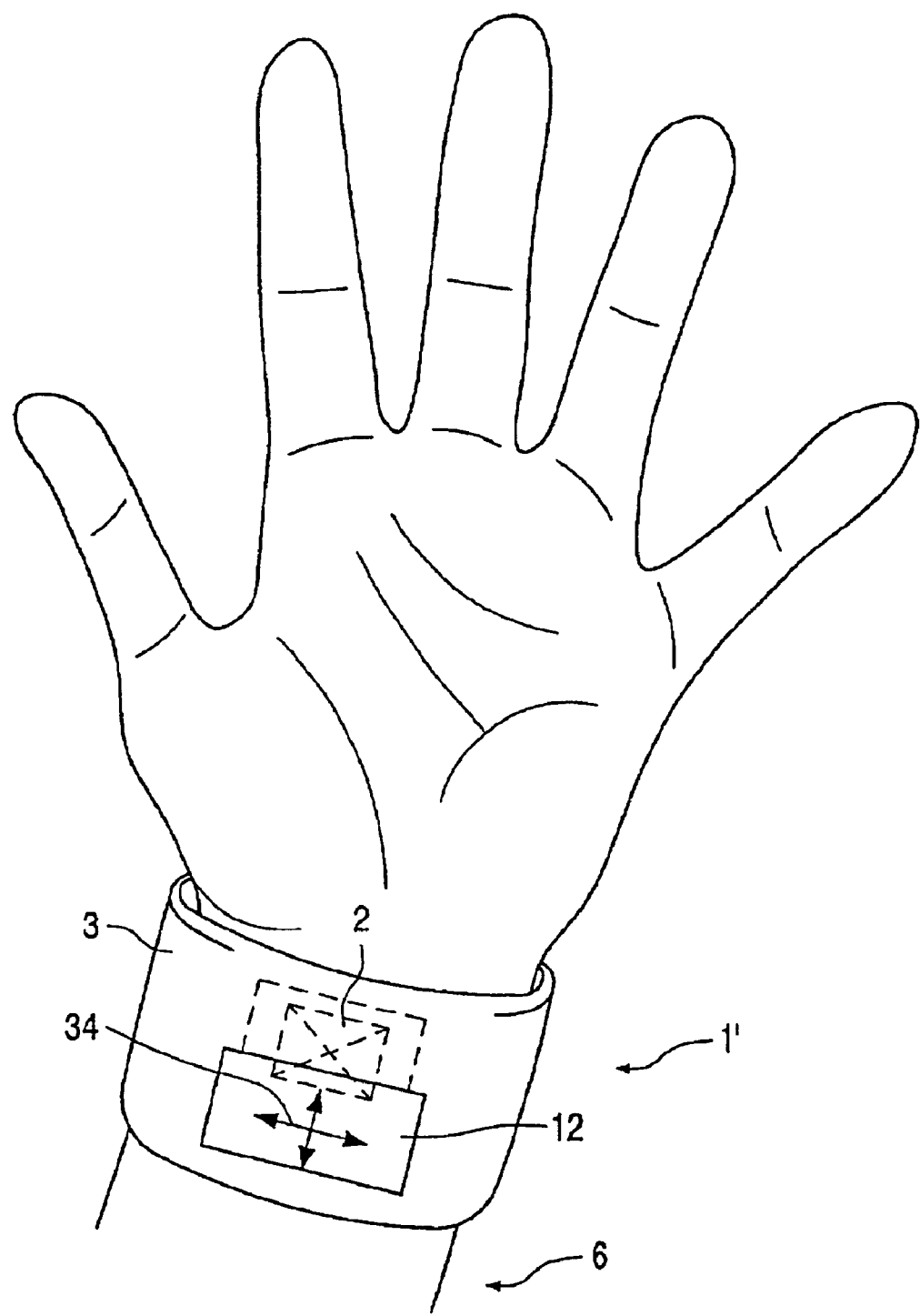
Figure 6:
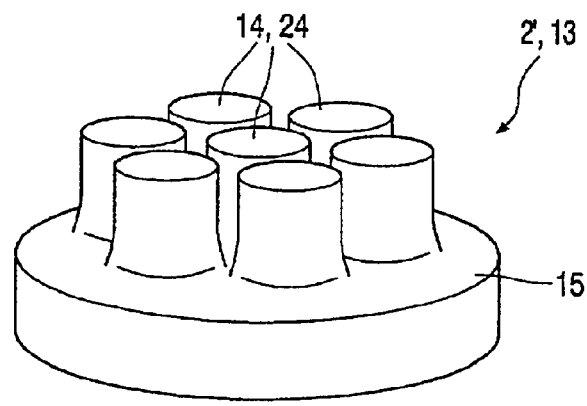
Figure 7:
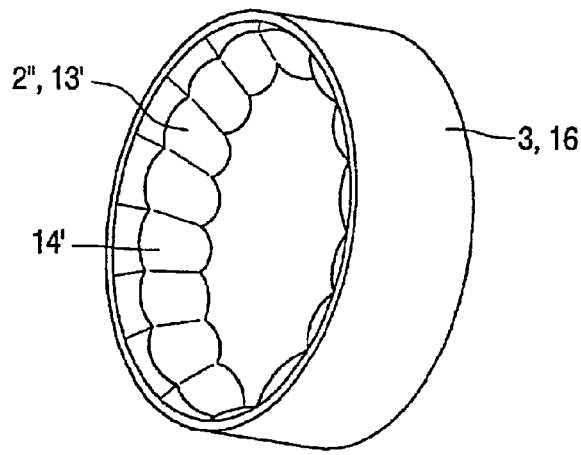
Figure 8:
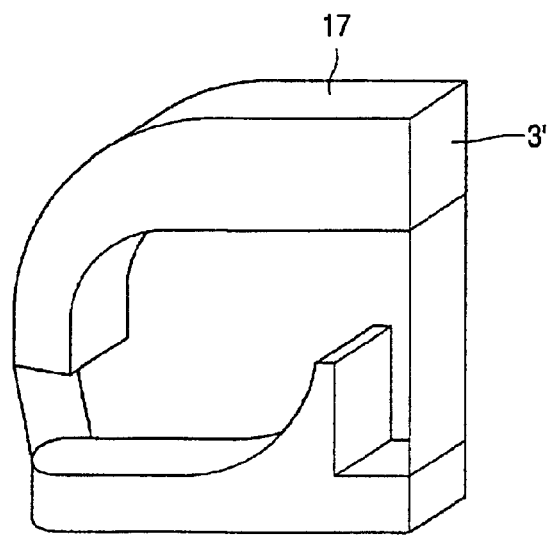

The invention will be described in more detail hereinafter with reference to the drawings, in which FIG. 1 is a perspective view of a first embodiment of a device according to the invention, FIG. 2 is a diagrammatic view of a cross-section of the device of FIG. 1 provided on a wrist of a living subject, taken on the line II—II, FIGS. 3a and 3b diagrammatically show a detector of the device of FIG. 1, and a detector of a second embodiment of a device according to the invention, respectively, FIG. 3c diagrammatically shows a cross-section of the detector of FIG. 3b, taken on the line IIIc—IIIc, FIG. 4 shows in functional blocks a processing of a signal detected by a detector into a feedback signal in the device of FIG. 1, FIG. 5 is a perspective view of a third embodiment of a device according to the invention, provided on a wrist of a living subject, FIG. 6 is a perspective view of a measuring unit of a fourth embodiment of a device according to the invention, FIG. 7 is a perspective view of a measuring unit of a fifth embodiment of a device according to the invention, and FIG. 8 is a perspective view of a carrier of a sixth embodiment of a device according to the invention.

FIGS. 1 and 2 show a first embodiment of a device 1 for monitoring a vital sign according to the invention, including a measuring unit 2 for measuring at least one physical quantity indicative of said vital sign at an area 8 overlying an artery 7 of a living subject. The measuring unit 2 is provided on a carrier 3 to be worn by the subject during operation, which carrier in this embodiment comprises a band 3' worn by the subject around a wrist 6. In this embodiment, the area overlying an artery where the measuring unit 2 measures the physical quantity is the area 8 overlying the radial artery 7 of the subject. Furthermore, a processing unit 4 for processing the measured physical quantity into a value for the vital sign is included in the device 1. The device 1 is provided with at least one detector 5 for detecting the position of the measuring unit 2 relative to the artery 7 of the subject during operation and for actuating a feedback signal in dependence on this position. In this way a user of the device 1 can move the device 1 relative to the artery until the correct position of the measuring unit 2 relative to said artery 7 is reached, reacting to the feedback signal generated by the detector 5 detecting the position of said artery 7. Thus a correct positioning of the measuring unit 2 relative to the artery is achieved in an easy manner. The detector 5 comprises at least one sensor, preferably chosen from a group comprising electro-optical sensors and ultrasound sensors, and preferably a plurality of sensors are provided in an array. One sensor in the array is pre-determined to actuate a feedback signal indicating that a correct position of the measuring unit 2 relative to the artery 7 has been reached, when it detects the presence of the artery 7. When the device 1 is placed on the artery 7 with its measuring unit 2, a number of sensors in the array will not detect the presence of the artery but at least one sensor will. Thus an indication can be given to the user through the sensors in which directions the device 1 should be shifted for the previously determined sensor to detect the presence of the artery, which indicates a correct positioning.

FIGS. 3a and 3b show a detector 5 of the device of FIG. 1, and a detector 5' of a second embodiment of a device according to the invention, respectively. The detectors 5 and 5' comprise a configuration of arrays of electro-optical sensors 10 with a light source 11, here a Light Emitting Diode. To prevent relative movement between the LED and the sensors, they are located on a rigid support 20. The distance between the LED and each sensor is preferably 2 to 5 mm for good operation. The sensors are separated from each other by a small wall 30 which extends perpendicularly from the rigid support 20, as can be seen in FIG. 3c, in order to avoid direct light reflections between the LED and the sensors.

The sensors 10 and the LEDs are further connected to a flexible printed circuit board which comprises the processing unit 4 and is not shown in any detail. During operation, each LED emits light to an area on which the measuring unit 2 contacts the wrist, which area produces a certain reflection of the light originating from the LED. When the user moves the device 1 relative to the wrist, a change in this reflection of light occurs when an artery is present beneath the detector, because the blood present in the artery absorbs a certain amount of the light. The electro-optical sensors 10 detect this change and actuate an output signal corresponding to it.

As can be seen in the diagram of FIG. 4, this output signal is directed to the processing unit 4. First it is amplified by an amplifier 41, after which a digital signal processing part 42 of the processing unit 4 processes the signal and estimates the location of the measuring unit 1 relative to the artery, based on the relative strengths of the signals of the sensors. Based on this estimation, a feedback signal Ufeedback is created and transmitted to the user by an audio or visual unit 43, to guide the user in positioning the measuring unit 2 correctly relative to the artery. It is noted that the configuration of the detector 5 and the number of sensors and light sources used in that configuration may be chosen freely, depending on the type of device they are applied in. For example, a combination of two of the detectors from FIG. 3a has been proven to offer good results in correctly positioning the measuring unit in a wrist blood pressure monitor relative to the radial artery of a subject.

It is further noted that the detector comprising electro-optical sensors together with the light source, as described in this embodiment, can fulfil a double function when applied in the known device for monitoring blood pressure as described in the prior art. On the one hand, the detector detects the position of the measuring unit relative to the artery of the subject during the placement of the device on the wrist and actuates a feedback signal according to this position. On the other hand, the detector can further serve to detect the blocking or unblocking condition of the artery, during the monitoring of blood pressure with the known device upon which detected condition the measuring unit measures the instantaneous value of each applied pressure pulse so as to provide a value of said subject's blood pressure through the processing unit.

FIG. 5 shows a third embodiment of a device 1' according to the invention in perspective view, provided on the wrist 6 of a person. In this embodiment, the feedback signal Ufeedback comprises a visual signal formed by directive arrows 34 on a display 12 which is attached to the carrier 3. In this way, the subject himself can easily read the directions on the display. He can easily adjust the position of the device relative to his wrist, following the arrows 34, thus adjusting the position of the measuring unit relative to the artery until the display confirms a correct position. It is noted that the feedback signal Ufeedback may alternatively comprise an audiosignal, for example beeping sounds during positioning and a ringing sound when a correct position of the measuring unit relative to the artery is reached.

FIG. 6 is a perspective view of a measuring unit 2' of a fourth embodiment of a device according to the invention. The measuring unit 2' in this embodiment comprises an inflatable cushion 13 for applying a pressure to said area overlying said artery of the subject. The cushion 13 can be inflated with, for example, air, but other gases and liquids may alternatively be used to inflate the cushion. The cushion 13 is connected to a unit for inflating and deflating the cushion, which is not further shown here. When applying a pressure by means of a cushion to such an area, the transmission of the pressure to the tissue to be pressurized is sometimes disturbed by the structure of the area, which structure comprises bones or tendons lying in the area. The cushion 13 is provided with a plurality of separately inflatable cushion parts 14, the cushion parts 14 each applying a local pressure to the area during operation. The cushion parts 14 enter between the bones and tendons in the area and the pressure thus is applied effectively to the tissue between these bones and tendons. In this embodiment, the cushion parts 14 comprise protuberances 24 projecting from a surface area 15 of the cushion practically perpendicularly to that surface area 15. The pressure is thus applied in an effective way by each of the protuberances 24, which bear a resemblance to fingers applying a pressure to certain areas.

FIG. 7 is a perspective view of a measuring unit 2" of a fifth embodiment of a device according to the invention. In this embodiment, the carrier 3 comprises an annular body 16 which can be closed during operation and in which the cushion 13', as described above for FIG. 6 and provided with a plurality of separately inflatable cushion parts 14', is provided along an entire inner wall of said body. This provision of cushion parts 14' along the inner wall of said body enables the cushion 13' to apply localized pressure to the entire periphery of the wrist 6 of a subject.

It is noted that a cushion of the kind as described above, i.e. a cushion comprising protuberances projecting from a surface area of the carrier in a direction practically perpendicular to that surface area, in itself is also usable in other devices for the monitoring of a vital sign in which the detector for positioning the measuring unit relative to the artery is not provided. For example, such a cushion may be used in the blood pressure monitor known from U.S. Pat. No. 4,660,566, instead of the flat cushion used therein.

FIG. 8 is a perspective view of a carrier of a sixth embodiment of a device according to the invention. In this embodiment, the carrier 3 comprises a annular body 17 which is entirely rigid. The annular body 17 may, for example, consist of a hard plastic, but other materials could alternatively be chosen. In this way, when a cushion in the device is to be inflated, the annular body forms a boundary for the level of expansion of the cushion, and thus prevents excessive expansion of the cushion which would hamper a good operation of the device. The rigid body 17 can be given a fixed shape, which may be chosen to fit specific subjects, so that the device may be adapted to certain specific user groups, such as children. Furthermore the shape may be adapted to the specific type of device for monitoring a vital sign in which it is used.

It is noted that a carrier of the kind as described above, i.e. a carrier comprising an annular body which is at least partly rigid, in itself is also usable in other devices for the monitoring of a vital sign, in which devices the detector for positioning the measuring unit relative to the artery is not provided. For example, such a carrier may be used in the blood pressure monitor known from U.S. Pat. No. 4,660,566, instead of the flexible band used therein.

Besides, a device for monitoring a vital sign which comprises both a carrier and a cushion as described above, but in which the detector for positioning the measuring unit relative to the artery is not provided, is also possible.

The devices described above are blood pressure monitors. It is noted that a detector for detecting the position of a measuring unit relative to an artery of a subject and for actuating a feedback signal representative of this position, a cushion with separately inflatable cushion parts, and an at least partly rigid annular body, may, individually or in any combination with each other, be advantageously used in other kinds of devices for monitoring a vital sign such as, for example, pulse oximetry monitors and heart rate monitors.

What is claimed is:

1. A device (1) for monitoring a vital sign of a living subject, comprising a measuring unit (2) for measuring at least one physical quantity indicative of said vital sign at an area (8) overlying an artery (7) of the subject, which measuring unit (2) is provided on a carrier (3) to be worn by the subject during operation, and a processing unit (4) for processing the measured physical quantity into a value for the vital sign, characterized in that the device (1) is provided with at least one detector (5) for detecting the position of the measuring unit (2) relative to the artery (7) of the subject during operation and for actuating a feedback signal (Ufeedback) in dependence on this position, characterized in that a plurality of sensors (10, 11) for detecting the presence of the artery (7) in the vicinity of the sensor (10, 11) are provided in an array.

2. A device (1) for monitoring a vital sign of a living subject, comprising a measuring unit (2) for measuring at least one physical quantity indicative of said vital sign at an area (8) overlying an artery (7) of the subject, which measuring unit (2) is provided on a carrier (3) to be worn by the subject during operation, and a processing unit (4) for processing the measured physical quantity into a value for the vital sign, characterized in that the device (1) is provided with at least one detector (5) for detecting the position of the measuring unit (2) relative to the artery (7) of the subject during operation and for actuating a feedback signal (Ufeedback) in dependence on this position, wherein the carrier (3) comprises an annular body (3') which is at least partly rigid, characterized in that the carrier (3) comprises an annular body (3") which is entirely rigid.

3. A device (1) for monitoring a vital sign of a living subject, comprising a measuring unit (2) for measuring at least one physical quantity indicative of said vital sign at an area (8) overlying an artery (7) of the subject, which measuring unit (2) is provided on a carrier (3) to be worn by the subject during operation, and a processing unit (4) for processing the measured physical quantity into a value for the vital sign, characterized in that the device (1) is provided with at least one detector (5) for detecting the position of the measuring unit (2) relative to the artery (7) of the subject during operation and for actuating a feedback signal (Ufeedback) in dependence on this position, characterized in that the measuring unit (2') comprises an inflatable cushion (13) for applying a pressure to said area (8) overlying said artery (7) of the subject, and the cushion (13) comprises a plurality of separately inflatable cushion parts (14).

4. A device as claimed in claim 3, characterized in that the cushion parts (14) comprise protuberances (24) which project from a surface area (15) of the carrier (3) in a direction practically perpendicular to said surface area.

5. A device as claimed in claim 3 or 4, characterized in that the carrier (3) comprises an annular body (16) which can be closed during operation, the cushion (13') being provided along an entire inner wall of said body (16).

6. A method for positioning a device for monitoring a vital sign of a living subject, the method comprising:
   operating a device, responsive to a first positioning of the device on a living measurement subject near an artery, wherein the device comprises:
   a carrier to be worn by the subject during operation;
   an array of sensors;
   a measuring unit for measuring at least one physical quantity indicative of said vital sign; and
   a processing unit for providing signals in a human understandable fashion, the signals including a value of the vital sign, responsive to the at least one physical quantity;
   detecting, using at least one of the sensors, a more precise position of the artery; and
   communicating, responsive to the more precise position of the artery, a necessary motion of the device to allow the measuring unit to be placed on top of the artery.

7. The method of claim 6, wherein the array comprises more than two separate sensors.

8. The method of claim 6, wherein the array comprises sensors arranged in a plurality of rows.

9. A method for positioning a device for monitoring a vital sign of a living subject, the method comprising:
   operating a device, responsive to a first positioning of the device on a living measurement subject near an artery, wherein the device comprises:
   a carrier to be worn by the subject during operation;
   an array of sensors;
   a measuring unit for measuring at least one physical quantity indicative of said vital sign; and
   a processing unit for providing signals in a human understandable fashion, the signals including a value of the vital sign, responsive to the at least one physical quantity;
   detecting, using at least one of the sensors, a more precise position of the artery; and
   communicating, responsive to the more precise position of the artery, a necessary motion of the device to allow the measuring unit to he placed on top of the artery,
   wherein communicating comprises supplying visible direction arrows on a user-visible surface of the carrier, which direction arrows indicate a desirable direction of motion for repositioning the device.

10. A method for positioning a device for monitoring a vital sign of a living subject, the method comprising:
   operating a device, responsive to a first positioning of the device on a living measurement subject near an artery, wherein the device comprises;
   a carrier to be worn by the subject during operation;
   an array of sensors;
   a measuring at least one physical quantity indicative of said vital sign; and
   a processing unit for providing signals in a human understandable fashion, the signals including a value of the vital sign, responsive to the at least one physical quantity;
   detecting, using at least one of the sensors, a more precise position of the artery; and communicating, responsive to the more precise position of the artery, a necessary motion of the device to allow the measuring unit to be placed on top of the artery.
   comprising responsive to the necessary motion, detecting a further more precise positioning of the artery using at least one different one of the array of sensors and iterating until a correct positioning is reached.

11. A blood pressure measuring device comprising
   a carrier to be worn by the subject during operation;
   an array of sensors for detecting an artery;
   a measuring unit for measuring at least one physical quantity indicative of blood pressure; and
   a processing unit for providing signals, the signals including
      a feedback signal, responsive to an output from the array of sensors, for enabling a user to reposition the device to place the measuring unit more nearly over the artery, and
      a blood pressure value, responsive to the at least one physical quantity and responsive to the output from the array of sensors indicating that the measuring unit is properly positioned over the artery.

12. A blood pressure measuring device comprising
   a carrier to be worn by the subject during operation;
   an array of sensors for detecting an artery;
   a measuring unit for measuring at least one physical quantity indicative of blood pressure; and
   a processing unit for providing signals, the signals including
      a feedback signal, responsive to an output from the array of sensors, for enabling a user to reposition the device to place the measuring unit more nearly over the artery, and
      a blood pressure value, responsive to the at least one physical quantity and responsive to the output from the array of sensors indicating that the measuring unit is properly positioned over the artery
   further comprising a user-readable display device displaying lighted arrows responsive to the feedback signal to indicate a desired direction of motion of the device.

* * * * *